United States Patent

Denny et al.

[11] Patent Number: 6,111,109
[45] Date of Patent: Aug. 29, 2000

[54] PROCESS FOR THE PREPARATION OF N-[2-(DIMETHYLAMINO)ETHYL]ACRIDINE-4-CARBOXAMIDE

[75] Inventors: William Alexander Denny; Swarnalatha Akuratiya Gamage; Julie Ann Spicer, all of Auckland, New Zealand; Michael Wright; David Frank Hayman, both of Slough, United Kingdom

[73] Assignee: Xenova Limited, Berkshire, United Kingdom

[21] Appl. No.: 09/284,570

[22] PCT Filed: Oct. 17, 1997

[86] PCT No.: PCT/GB97/02884

§ 371 Date: Jun. 18, 1999

§ 102(e) Date: Jun. 18, 1999

[87] PCT Pub. No.: WO98/17649

PCT Pub. Date: Apr. 30, 1998

[30] Foreign Application Priority Data

Oct. 18, 1996 [GB] United Kingdom .................. 9621795
Dec. 20, 1996 [GB] United Kingdom .................. 9626457

[51] Int. Cl.[7] .................. C07D 219/02; C07D 219/08; C07D 219/04; C07D 219/10
[52] U.S. Cl. .................. 546/102; 546/103; 546/104; 546/105
[58] Field of Search .................. 546/102, 103, 546/104, 105

[56] References Cited

U.S. PATENT DOCUMENTS

| | | | |
|---|---|---|---|
| 3,686,180 | 8/1972 | Sutton et al. ........... | 546/102 |
| 4,590,277 | 5/1986 | Atwell et al. ........... | 546/105 |

FOREIGN PATENT DOCUMENTS

| | | |
|---|---|---|
| 0098 098 | 1/1984 | European Pat. Off. . |
| 0098098 | 1/1984 | European Pat. Off. . |

OTHER PUBLICATIONS

Potential Anti–tumor Agents ; J. Med. Chem. !987 vol. 30 pp. 664–669; Graham J. Atwell, Aug. 20, 1986.
Facile Reduction of Carboxylic Acid . . . ; Synlett Rajiv et al; pp. 839–840, Mar. 15, 1995.

Rewcastle et al, "The synthesis of 9–oxo–9,10-dihydroacridine–4–carboxylic acids via the Jourdan–-Ullman reaction of anthranilic acids and methyl 2–iodo-benzoates", *Synthetic Communications*, vol. 17, No. 3, 1987, pp. 309–317.

Atwell et al, "Potential antitumor agents.50.Invivo solid–tumor activity of derivatives of N–[2–(dimethylamino)ethyl] acridine–4–carboxamide", *Journal of Medicinal Chemistry*, vol. 30, No. 4, 1987, Washington, U.S., pp. 664–669.

Sharma et al, "Facile reduction of carboxylic acid imidazolides to primary alcohols in the presence of water", *Synlett*, No. 8, Aug. 1995, Stuttgart, DE, pp. 839–840.

Gamage et al, "A new synthesis of substituted acridine–4–carboxylic acids and the anticancer drug N–[2–(dimethylamino)ethyl] acridine–4–carboxamide (DACA)", *Tetrahedron Letters*, vol. 38, No. 4, Jan. 27, 1997, Oxford, GB, pp. 699–702.

*Primary Examiner*—Alan L. Rotman
*Assistant Examiner*—Rita Desai
*Attorney, Agent, or Firm*—Nixon & Vanderhye

[57] ABSTRACT

A process for producing an acridine carboxamide of formula (I):

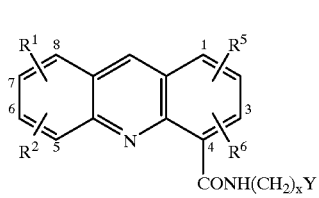

wherein each of $R^1$, $R^2$, $R^5$ and $R^6$, which may be the same or different, is H or an organic subsituent, x is from 1 to 6 and Y is N(R)2 wherein R is $C_1$–$C_6$ alkyl, or a pharmaceutically acceptable salt thereof.

11 Claims, No Drawings

PROCESS FOR THE PREPARATION OF N-[2-(DIMETHYLAMINO)ETHYL]ACRIDINE-4-CARBOXAMIDE

This is a 35 U.S.C. § 371 of PCT/GB97/02884 filed Oct. 17, 1997.

The present invention relates to a new process for the production of the anti-cancer drug N-[2-(dimethylamino)ethyl]acridine-4-carboxamide and derivatives thereof.

The acridine derivative N-[(2-dimethylamino)ethyl] acridine-4-carboxamide, known as DACA, is a new DNA-intercalating agent with inhibitory activity against the enzymes topoisomerase I and topoisomerase II (Schneider et al, Eur. J. Cancer Clin. Oncol, 1988, 24 1783 and Finlay, et al Eur J. Cancer 1996, 32A 708). It has a wide spectrum of activity against solid tumours in animals and is relatively unaffected by P-glycoprotein-mediated multidrug resistance (Atwell et al, J. Med Chem, 1987, 30, 664, Baguley et al, Cancer Chemother. Pharmacol 1995, 36, 244 and Finlay et al Cancer Chemother. Pharmacol. 1993, 31,401). Certain analogues of DACA have been reported, and many have shown significant activity in a mouse solid tumour (Atwell et al, ibid).

The known process for producing DACA, reported by twell et al, ibid, is shown in Scheme 1.

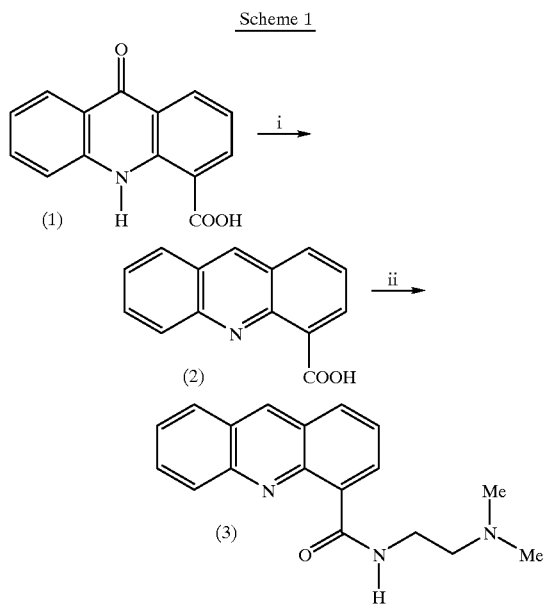

Step (i) comprises reduction of the acridone (1) by treatment with aluminium/mercury amalgam in the presence of KOH in aqueous ethanol under reflux, followed by reoxidation of the resulting acridan with $FeCl_3$, to give the intermediate acridine carboxylic acid (2). Step (ii) comprises treatment of the acid (2) with 1,1-carbonyldiimidazole (CDI) and dimethylformamide, followed by N,N-dimethylethylenediamine.

Various disadvantages are associated with this process. One is that the reductive conditions required in step (i) are harsh. This limits the scope of the process and makes it unsuitable for the production of certain analogues of DACA which bear reduction-sensitive substituents on the acridine nucleus. For instance, dechlorination has been observed when the process has been applied to the production of chloro-substituted derivatives of DACA. Another disadvantage of the known process is that the intermediate acridine carboxylic acids (2) have severe lachrymatory and sternutatory properties, which limit their use.

It has now been found that DACA and derivatives thereof can be produced by a process which comprises cyclising an aldehyde precursor which includes an esterified, rather than a free, carboxylic acid functional group and then subjecting that esterified group in the cyclised product directly to treatment with a primary alkyl amine. If desired the esterified group in the cyclised product can first be hydrolysed to generate a free carboxylic acid function, which is then treated with the primary alkyl amine in the presence of a suitable coupling agent. The aldehyde precursor is readily produced by oxidation of the corresponding alcohol, which in turn is produced by mild reduction of the corresponding carboxylic acid via an imidazolide intermediate.

Accordingly, the present invention provides a process for producing an acridine carboxamide of formula (I):

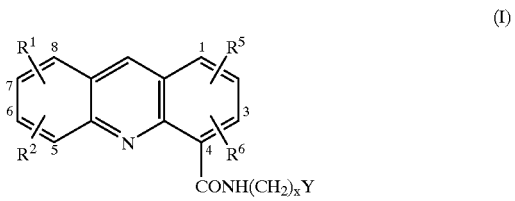

wherein each of $R^1$, $R^2$, $R^5$ and $R^6$, which may be the same or different, is H, $C_1$–$C_6$ alkyl, $C_1$–$C_6$ alkoxy, aryloxy, aralkyloxy, halogen, phenyl, $CF_3$, $NO_2$, $NH_2$, $N(R)_2$, NHCOR, NHCOOR, $NHR^4$, OH, SH, SR or S $(R)_2$, wherein $R^4$ is H, COR, $SO_2R$, COPh, $SO_2Ph$ or $C_1$–$C_6$ alkyl unsubstituted or substituted by OH or amino, and R is $C_1$–$C_6$ alkyl; or $R^1$ and $R_2$, or $R_5$ and $R_6$, together form a methylenedioxy group; x is an integer of 1 to 6 and Y is $N(R)_2$ as defined above; or a pharmaceutically acceptable salt thereof; which process comprises:

(a) cyclising a compound of formula (II)

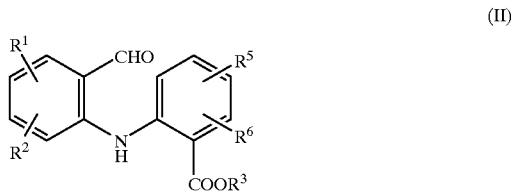

wherein $R^1$, $R^2$, $R^5$ and $R^6$ are as defined above and $R^3$ is $C_1$–$C_6$ alkyl, aryl or aryl-$C_1$–$C_3$-alkyl, by treatment with a Lewis acid in an organic solvent, to obtain a compound of formula (III):

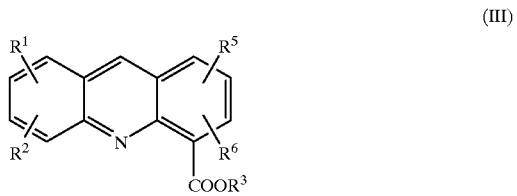

wherein $R^1$, $R^2$, $R^3$, $R^5$ and $R^6$ are as defined above; and (b) treating either (i) the compound of formula (III) as defined above with a primary alkylamine of formula (IV)

wherein X and Y are as defined above, or (ii) the carboxylic acid obtainable by hydrolysing the compound of formula (III) as defined above, under basic conditions, with a primary alkyl amine of formula (IV) as defined above in the presence of a suitable coupling agent, to obtain a compound of formula (I) as defined above; and (c) if desired, converting one compound of formula (I) into another compound of formula (I), and/or converting a compound of formula (I) into a pharmaceutically acceptable salt thereof.

In a preferred embodiment of this process $R^1$, $R^2$, $R^5$ and $R^6$ in formula (II) are H, and in formula (IV) x is 2 and Y is $NMe_2$. The resulting compound of formula (I) is then N-[(2-dimethylamino)ethyl]acridine-4-carboxamide (DACA).

Any suitable Lewis acid may be employed in step (a). An example is trifluoroacetic acid, which is used under nitrogen at room temperature. Alternatively step (a) may be performed by treatment of the compound of formula (II) with either borontrifluoride or a suitable complex thereof in a suitable solvent. Suitable complexes include the acetic acid complex. In one embodiment, a slight excess of 1 ⅓ moles of $BF_3$ (the stoichiometric amount) would be used, for instance 2 molar equivalents. The $BF_3$ is typically used in the form of its etherate $BF_3O(Et)_2$. Suitable solvents for use with $BF_3O(Et)_2$ include EtOAc and $CH_2Cl_2$. The compound of formula (III) is then obtained in either case in the form of its tetrafluoroborate salt of formula (IIIa):

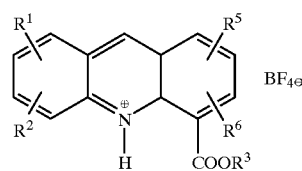

(IIIa)

wherein $R^1$, $R^2R^3$, $R^5$ and $R^6$ are as defined above.

When $BF_3$ is used, generation of the tetrafluoroborate salt (IIIa) can be represented as follows:

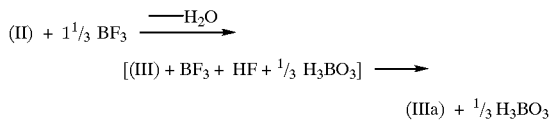

The tetrafluoroborate salt of formula (IIIa) precipitates out from the reaction mixture and can be removed easily by filtration. Addition of an inorganic base, for instance sodium carbonate, and a solvent such as ethyl acetate or dichloromethane to the filtered solid generates the compound of formula (III). This can then be treated further with an amine of formula (IV). Advantages of this procedure are that the tetrafluoroborate salt is produced in almost quantitative yield, and can readily be subjected to further reaction without the need to separate excess reagents or side products. This facilitates operation of the process of the invention on an industrial scale, particularly since through-put can be increased.

It may in some cases be desirable to hydrolyse the compound of formula (III) to the corresponding acid prior to treatment with the amine of formula (IV) in step (b). This may be, for example, if the compound of formula (III) itself is unstable to oxidation. The hydrolysis is carried out under mild basic conditions, for instance by treatment with an alkali metal hydroxide (e.g. NaOH or KOH) in a solvent such as ethanol. Any suitable coupling agent may be used in the reaction of the acid with the amine of formula (IV) in step (b), for example 1,1'-carbonyldiimidazole.

The compound of formula (II) is produced by oxidising the corresponding alcohol of formula (V):

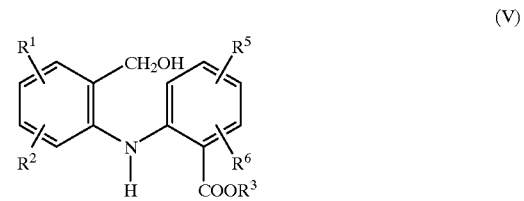

(V)

wherein $R^1$, $R^2$, $R^3$, $R^5$ and $R^6$ are as defined above.

The oxidation is performed under any suitable oxidising conditions. Manganese (IV) oxide ($MnO_2$), for instance in solid form in a polar solvent such as ethyl acetate or acetone, is a preferred oxidising agent. $MnO_2$ may, for instance, be added as a suspension in acetone to the alcohol of formula (V) and allowed to react at room temperature. The reaction then typically takes several days, for instance 2 or 3 days, to reach completion. Alternatively, a mixture of the alcohol of formula (V) and $MnO_2$ in ethyl acetate may be ref luxed together, for example overnight.

The alcohol of formula (V) is produced by (a) treating a compound of formula (VI):

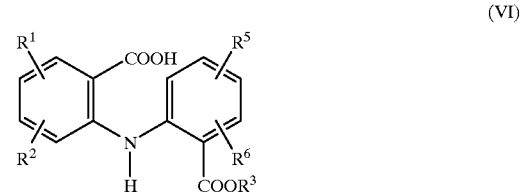

(VI)

wherein $R^1$, $R^2$, $R^3$, $R^5$ and $R^6$ are as defined above, with 1,1'-carbonyldiimidazole in a polar solvent, to obtain a compound of formula (VII):

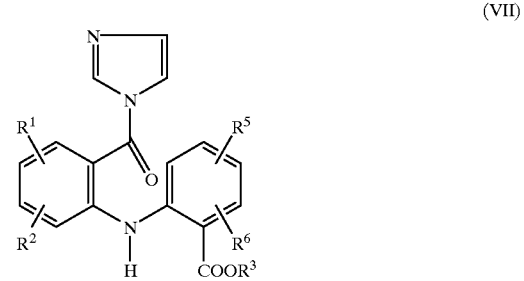

(VII)

wherein $R^1$, $R^2$, $R^3$, $R^5$ and $R^6$ are as defined above, and (b) reducing the imidazolide of formula (VII) as defined above.

In step (a) above the polar organic solvent may be, for instance, THF. The reactants are typically stirred at room temperature until the reaction is complete. In step (b) the reduction is typically performed by treatment of the compound of formula (VII) with an excess of a metal-based reducing agent, for instance sodium borohydride. In this case the solution which results from step (a) may suitably be added to a stirred suspension of sodium borohydride in water.

The use of the intermediate imidazolide of formula (VII) allows the reduction of carboxylic acids of formula (VI) to alcohols of formula (V) to take place relatively easily under mild conditions.

The compounds of formula (VI) are known compounds or may be produced by known methods, for instance by heating together an anthranilic acid of formula (VIII):

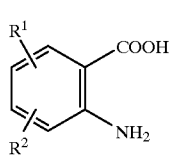

(VIII)

wherein $R^1$ and $R^2$ are as defined above, and a 2-iodobenzoic acid ester of formula (IX):

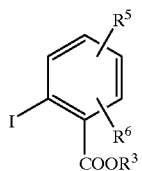

(IX)

wherein $R^3$, $R^5$ and $R^6$ are as defined above, in the presence of a copper catalyst and a base in a polar solvent.

The copper catalyst suitably comprises a copper (I) halide and copper powder. The polar solvent may be, for instance, ethylene glycol or butane-2,3-diol. Any suitable base may be used, for instance N-ethyl morpholine.

In the compounds of formula (I) produced by the process of the invention, the substituents $R^1$ and $R^2$ may occupy any one of ring positions 5 to 8, and substituents $R^5$ and $R^6$ may occupy any one of ring positions 1 to 4, in the tricyclic chromophore. Thus $R^1$ and $R^2$ may each be bonded to any one of the ring positions in the starting compounds and intermediates of formulae (III) and (V) to (VIII) which correspond to positions 5 to 8 of the final compounds of formula (I). Similarly, $R^5$ and $R^6$ may be bonded to any one of the ring positions in the starting materials and intermediates of formulae (III) and (V) to (VIII) which correspond to positions 1 to 4 of the final compounds of formula (I).

In one preferred series of compounds $R^5$ and $R^6$ are both H. In this series the compounds are of the general formula (Ia):

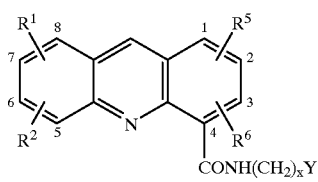

(Ia)

wherein $R^1$, $R^2$, x and y are as defined above for formula (I). Formula (Ia) is thus a preferred embodiment of formula (I). Typically one of $R^1$ and $R^2$ is hydrogen and the other is hydrogen or a substituent as defined above for formula (I) bonded at any one of ring positions 5 to 8.

In a preferred series of compounds of formula (I) each of $R^1$ and $R^2$, which may be the same or different, is H, $C_1$–$C_6$ alkyl, $C_1$–$C_6$ alkoxy, halogen, phenyl, $CF_3$, $NO_2$, $NH_2$, $N(R)_2$ as defined above or OH, x is an integer of 1 to 3 and Y is $N(R)_2$ as defined above.

Typically $R^1$ is H and $R^2$ is H or a substituent other than H bonded at position 5, 6 or 7 of the acridine nucleus in formula (I). For instance, $R^1$ is H and $R_2$ is at position 5 and is $C_1$–$C_6$ alkyl, $CF_3$, phenyl, halogen or a group $N(R)_2$; or $R^1$ is H and $R^2$ is at position 6 and is halogen, $CF_3$ or $N(R)_2$ as defined above; or $R^1$ is H and $R^2$ is at position 7 and is $C_1$–$C_6$ alkyl, phenyl, OH, halogen, $CF_3$ or $N(R)_2$.

Alternatively $R^1$ is other than hydrogen. For instance, when $R^2$ is at position 5 as defined above, $R^1$ is at position 6, 7 or 8, preferably 6 or 7, and is $C_1$–$C_6$ alkyl, $C_1$–$C_6$ alkoxy, halogen, phenyl, $CF_3$, $NO_2$, $NH_2$, $N(R)_2$ as defined above, or OH. When $R^2$ is at position 6 as defined above $R^1$ is at position 5, 7 or 8, preferably 5 or 7, and is $C_1$–$C_6$ alkyl, $C_1$–$C_6$ alkoxy, halogen, phenyl, $CF_3$, $NO_2$, $NH_2$, $N(R)_2$ or OH. When $R^2$ is at position 7 as defined above, $R^1$ is at position 5, 6 or 8, preferably 5 or 6, and is $C_1$–$C_6$ alkyl, $C_1$–$C_6$ alkoxy, halogen, phenyl, $CF_3$, $NO_2$, $NH_2$ $N(R)_2$ or OH.

A $C_1$–$C_6$ alkyl group may be linear or branched, and is, for example $C_1$–$C_4$ alkyl such as methyl, ethyl, n-propyl, i-propyl, n-butyl, s-butyl or t-butyl. A $C_1$–$C_6$ alkoxy group may also be linear or branched, and is, for example, $C_1$–$C_4$ alkoxy such as methoxy, ethoxy, n-propoxy, i-propoxy, n-butoxy, s-butoxy or t-butoxy. A halogen is, for example, fluorine, chlorine, bromine or iodine. An aryl group is, for example, a $C_6$–$C_{12}$ aryl group such as phenyl or naphthyl. The aryl moiety in an aryl-$C_1$–$C_3$-alkyl, aralkyloxy or aryloxy group may be a $C_6$–$C_{12}$ aryl group, for instance phenyl or naphthyl. Examples of a aryl-$C_1$–$C_3$-alkyl group thus include phenyl-$C_1$–$C_3$-alkyl groups, such as benzyl and phenylethyl.

The compounds of formula (I) may be converted into pharmaceutically acceptable acid addition salts, by conventional methods. For instance, the acid addition salts may be prepared by contacting the free base with an appropriate amount of the desired acid in a conventional manner. Suitable salts include salts with both organic and inorganic acids. Examples of suitable acids are hydrochloric, sulfuric, phosphoric, acetic, citric, oxalic, malonic, salicylic, maleic, fumaric, succinic, ascorbic, methanesulfonic and the like. Depending on structure, and on the conditions, the compounds may form multicationic forms.

The optional conversion of a compound of formula (I) into another compound of formula (I) may be carried out by conventional methods. For instance, a fluoro group in a compound of formula (I) may be replaced by an amino or thiol group to give an amine or thioether, respectively; a thiol group in a compound of formula (I) may be alkylated to give a thioether; an amino group may be acylated to give an N-acetyl group; and a nitro group may be reduced to give an amine. These are all routine conversions in organic chemistry.

The amines of general formula (IV) are known compounds, and are commercially available or preparable by methods described in the literature. Specific examples of such compounds include $NH_2(CH_2)_2NMe_2$ [x is 2 and Y is $N(CH_3)_2$].

The compounds of formula (I) and their salts produced by the process of the invention may be formulated for use as a pharmaceutical or veterinary composition. The process of the present invention as defined above may therefore further comprise formulating a compound of formula (I) or a pharmaceutically acceptable salt thereof with a pharmaceutically or veterinarily acceptable carrier or diluent to form a pharmaceutical or veterinary composition. The composition is typically prepared following conventional methods such that it is suitable for administration to a human or animal patient.

The composition may be formulated in a variety of dosage forms, for example for oral administration such as in the form of tablets, capsules, sugar- or film-coated tablets, liquid solutions or suspensions, or for parenteral administration, for example intramuscularly, intravenously or subcutaneously. The compounds of formula (I) may therefore be formulated for injection or infusion.

For example, the solid oral forms may contain, together with the active compound, diluents, such as lactose, dextrose, saccharose, cellulose, corn starch or potato starch; lubricants such as silica, talc, stearic acid, magnesium or calcium stearate and/or polyethylene glycols; binding agents such as starches, arabic gums, gelatin, methylcellulose, carboxymethylcellulose, or polyvinyl pyrrolidone; disintegrating agents such as starch, alginic acid, alginates or sodium starch glycolate; effervescing mixtures, dye-stuffs; sweeteners; wetting agents such as lecithin, polysorbates, laurylsulphates. Such preparations may be manufactured in known manner, for example by means of mixing, granulating, tabletting, sugar coating, or film-coating processes.

Liquid dispersions for oral administration may be syrups, emulsions and suspensions. The syrups may contain as carrier, for example, saccharose or saccharose with glycerol and/or mannitol and/or sorbitol. In particular a syrup may contain as carrier, for example, saccharose or saccharose with glycerol and/or mannitol and/or sorbitol. In particular a syrup for diabetic patients can contain as carriers only products, for example sorbitol, which do not metabolise to glucose or which only metabolise a very small amount to glucose. The suspensions and the emulsions may contain as carrier, for example a natural gum, agar, sodium alginate, pectin, methylcellulose, carboxymethylcellulose or polyvinyl alcohol.

Suspensions or solutions for intramuscular injections may contain, together with the active compound, a pharmaceutically acceptable carrier such as sterile water, olive oil, ethyl oleate, glycols such as propylene glycol, ad if desired, a suitable amount of lidocaine hydrochloride. Typically the compounds of formula (I) are formulated as aqueous solutions of hydrochloride or other pharmaceutically acceptable salts. Solutions for intravenous injection or infusion may contain a carrier, for example, sterile water which is generally Water for Injection.

The invention will be further described in the Examples which follow:

EXAMPLE 1

Preparation of Methyl 2-[N-(2-carboxyuhenyl) amino]benzoate.

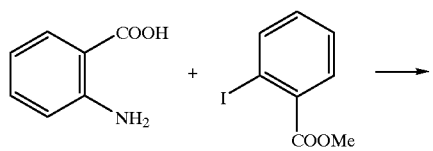

-continued

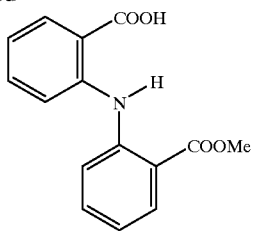

A mixture of anthranilic acid (16.48 g, 120 mmol), methyl 2-iodobenzoate (39.3 g, 150 mmol), N-ethyl morpholine (38.1 ml; 34.5 g, 300 mmol), ethylene glycol (120 ml), cuprous chloride (3 g) and copper powder (99%; 0.6 g) was stirred in an oil bath at 140° C. for 6 hours (internal temperature, ca 130° C.). The reaction mixture was cooled and slowly poured into a stirred mixture of ethyl acetate (300 ml) and 1M hydrochloric acid (300 ml) after which the mixture was filtered to remove insoluble interfacial material. The bed was washed with ethyl acetate (200 ml).

After separation of the organic phase from the filtrate, the aqueous layer was then extracted in succession with the ethyl acetate washes (2×100 ml) of the above filter bed. The combined organic extracts were stirred with activated carbon (3 g) and filtered. The filtrate was extracted with ca 1.5% aqueous ammonia solution (1×400 ml and 2×150 ml). The combined ammoniacal extracts were added slowly to a stirred excess of 1M hydrochloric acid and the product was collected by filtration, washed with hot water (3×100 ml) and pulled dry (wet weight, ca 60 g). After drying in vacuo at 55° C., the title compound was obtained (27.8 g. 85.4%). (Purity by hplc ~90% a/a; major impurity was the corresponding dicarboxylic acid). mp196–198° C. $^1$HNMR (CDCl$_3$)δ3.93 (3,s COOMe), 6.92 (2H, m, J=7.5, H-4, H-4'), 7.26 (s, solvent CHCl$_3$), 7.38 (2H, m,H-5, H-5'), 7.51 (2H, br.t, J=8.9, H-6, H-6'), 7.98 (1H,dd, J=7.9 and 1.1, H-3'), 8.09 (1H, J=7.9, H-3), 10.82 (1H,br.s,NH).

EXAMPLE 2

Preparation of Methyl 2-[N-(2-hydroxymethyl) phenylamino]benzoate.

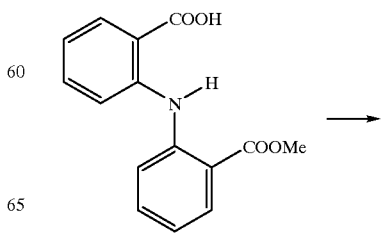

9

-continued

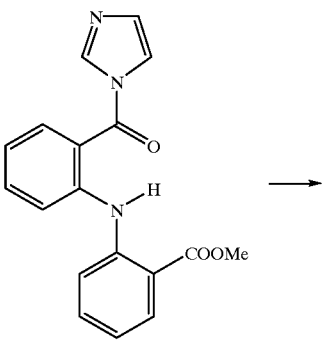

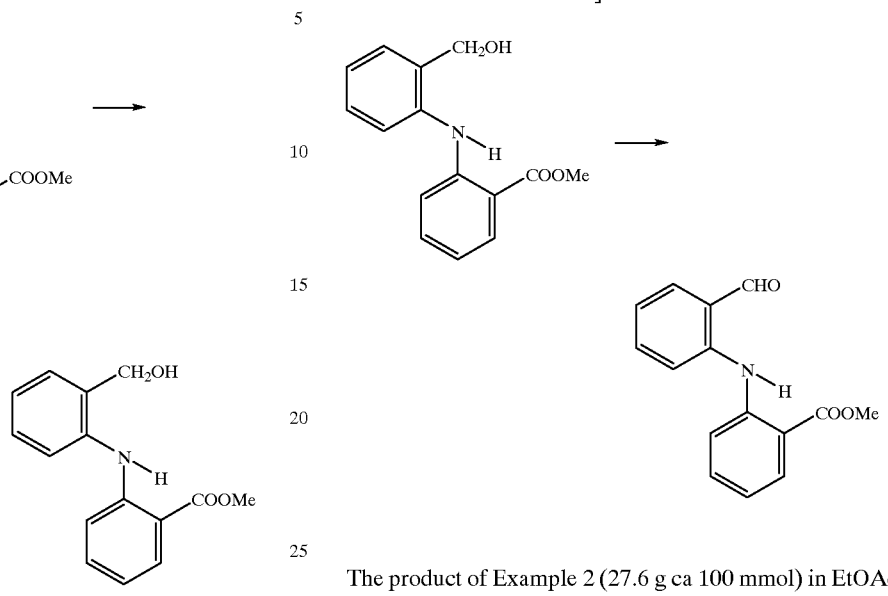

1,1'-Carbonyl diimidazole (19.5 g, 120 mmol) was added to the product produced in Example 1, (27.1 g, 100 mmol) in THF (hplc grade, 270 ml) and the mixture was stirred overnight at room temperature to give a light brown solution of the imidazolide intermediate. Tlc (SiO$_2$: 10% MeOH/CH$_2$Cl$_2$ with visualisation under UV at 254 nm) indicated the reaction was complete.

This solution was added over 30 minutes to a stirred suspension of sodium borohydride (12.5 g, 330 mmol) in water (375 ml). Initially, a yellow gum deposited which, by the end of the addition, had changed to a greyish yellow suspension and the temperature was 37° C. Tlc (SiO$_2$:EtOAc with visualisation under UV at 254 nm) indicated the reduction was complete. After stirring the suspension for a further 30 min, the excess sodium borohydride was destroyed by the addition of conc. HCl (35 ml) keeping the temperature below 30° C. by means of an ice bath. The pH of the mixture was ca 7. EtOAc (300 ml) and saturated sodium hydrogen carbonate solution (200 ml) was added and the mixture was stirred for a short time after which the organic phase was separated. (volume of discarded aqueous phase, 690 ml). The pale yellow organic solution was washed with brine (100 ml) separated and concentrated in vacuo. Re-evaporation from EtOAc (3×100 ml) gave the title compound (27.6 g>100%) as a yellowish brown oil, Hplc ca 90% a/a. A sample slowly crystallised on storage, mp 69–71° C. $^1$H NMR (CDCl$_3$)δ1.93 (br.s,1H, OH), 3.91 (s,3H, COOCH$_3$), 4.72 (s,2H, CH$_2$OH), 6.74 (ddd, J=8.0, 7.0, 1.1 Hz, 1H, H-5), 7.08–7.44 (m,6H,H-3,3',4,4',5',6'), 7.97 (dd, J=8.0, 1.6 Hz,1H, H-6), 9.59 (br.s, 1H, NH).

10

EXAMPLE 3

Preparation of Methyl 2-[N-(2-formyl)phenyl amino]benzoate

The product of Example 2 (27.6 g ca 100 mmol) in EtOAc (300 ml) was stirred with manganese (IV) oxide (<5 micron, activated ~85% MnO$_2$). (55 g, 2 wts) and refluxed overnight (17 h). Tlc (SiO$_2$:EtOAc) visualised under UV at 254 nm (in daylight the aldehyde can be seen as a yellow spot) indicated complete reaction. Activated charcoal (2.7 g) and Kieselguhr (2.7 g) were added to the warm mixture which was stirred for 30 minutes and filtered through a Kieselguhr bed. The bed was washed with EtOAc (2×100 ml).

The bright yellow filtrate was carefully concentrated in vacuo to half volume, removed from the evaporator and washed with water (50 ml). The organic phase was separated, concentrated in vacuo to a low volume (wt,47 g) when crystallisation of the product started and the residue set to an intense yellow solid. Hexane (200 ml) was added with stirring to break up the crystalline mass and after 1 hour the product was filtered, washed with hexane and dried in vacuo at 40° C. to give the title compound (19.6 g, 76.7%) HPLC 94.5% a/a. mp 110–112° C. $^1$H NMR(CDCl$_3$)δ3.95 (s, 3H, COOCH$_3$), 6.95–7.03 (m, 2H, H-4',5), 7.41–7.45 (m,2H,H-5'6), 7.50 (br d, J=8.5 Hz, 1H, H-3 or H-6'), 7.61 (br d, J=8.2 Hz, 1H, H-6' or H-3), 7.65 (dd, J=7.7, 1.7 Hz, 1H, H-3'), 8.01 (dd, J=7.9, 1.7 Hz, 1H, H-6), 10.00 (s, 1H, CHO) 11.26 (br s, 1H, NH)

EXAMPLE 4

Preparation of Methyl acridine-4-carboxylate.

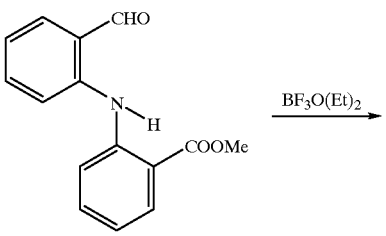

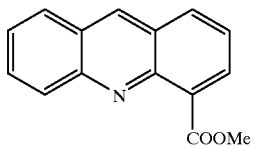

The aldehyde produced in Example 3 (12.75 g, 50 mmol) in degassed ethyl acetate (250 ml) was stirred under nitrogen and borontrifluoride acetic acid complex (25 ml, 33.8 g, 180 mmol) was added over 15 minutes. Before the addition was complete, the tetrafluoroborate salt began to crystallise as an orange solid. The mixture was left to stir under nitrogen at room temperature overnight. The thick orange precipitate was removed by filtration, washed with EtOAc (20 ml), hexane (50 ml) and pulled dry on the filter. (20 g. ca 92% pure by Hplc).

This solid was added to a mixture of EtOAc (250 ml) and saturated sodium carbonate solution (150 ml). The pale yellow organic layer was separated and washed with saturated brine solution (30 ml). Tlc (SiO$_2$: 10% MeOH in CH$_2$Cl$_2$ visualised under UV at 254 nm) showed essentially one spot. The organic solution was evaporated in vacuo to give the title compound (11.5 g, 97%) as a pale yellow oil which readily crystallised. HPLC indicated this was ca 90% pure. The material was used without further purification for the preparation of DACA. $^1$H NMR (CDCl$_3$)δ4.12 (s, 3H,COOCH$_3$), 7.53–7.58 (m,2H, H-2 and H-6 or H-7), 7.79 (ddd, J=8.8, 6.6, 1.4 Hz, 1H, H-7 or H-6), 8.00 (dd, J=8.0, 1.0 Hz, 1H, H-1) 8.12–8.14 (m,2H, H-5,8), 8.30 (dd, J=8.7, 0.9 Hz, 1H, H-3), 8.80 (s, 1H, H-9).

EXAMPLE 5

Preparation of N-[2-(dimethylamino)ethyl]acridine-4-carboxamide (DACA).

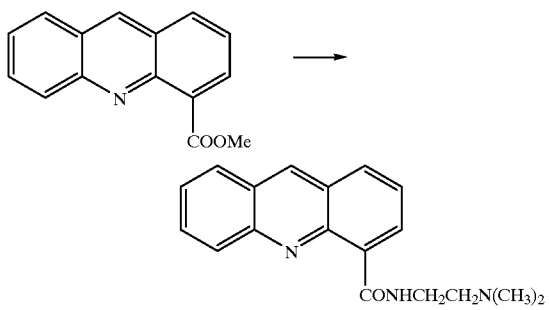

Methyl acridine-4-carboxylate produced as in Example 4, (11.2 g, 47 mmol) was diluted with N,N-dimethyl ethylenediamine (20 ml, 16.2 g, 184 mmol) and the solution was distilled down on a rotary evaporator to remove traces of residual EtOAc (loss in wt. ca 1.5 g). The mixture was then heated under nitrogen in an oil bath at 120° C. for 7 hours and left to cool over night in the bath. The mixture was dissolved in toluene (50 ml) and concentrated to a gum in vacuo.

The residue was dissolved in EtOAc (150 ml) and washed with 1M aqueous sodium carbonate solution (2×100 ml). The organic layer was separated, stirred with activated charcoal (1.5 g) and Kieselguhr (1.5 g), and filtered through a Keiselguhr bed. The bed was washed with EtOAc and the filtrate and washes were concentrated in vacuo to a yellowish brown oil which rapidly crystallised to a buff solid which was triturated with hexane (100 ml) and filtered to give title compound as a pale buff solid, washed with hexane (50 ml) and dried in vacuo at 40° C. (10.4 g, 75.4%)HPLC, 90–95% a/a, mp 105–108° C. $^1$HNMR (DMSO)δ2.34 (6H,s, N(CH$_3$)$_2$), 2.58 (2H,t, J=6.1, CH$_2$N(CH$_3$)$_2$), 3.61 (2H, m, J=11.2 and 6.0, CONHCH,), 7.67 (1H, m, J=7.1, 6.4 and 0.7, H-7), 7.71 (1H,dd, J=8.3 and 7.1, H-2), 7.95 (1H, m, J=7.7, 6.7 and 1.4, H-6) 8.18 (1H, dd, J=8.2 and 1.3, H-8), 8.18 (1H,dd, J=8.9 and 0.8, H-5), 8.31 (1H,dd, J=8.4 and 1.5, H-1), 8.74 (1H,dd, J=7.1 and 1.6, H-3), 9.23 (1H, s, H-9), 11.73 (1H,br.t, J=4.7, CONH).

EXAMPLE 6

Preparation of -[2-(Dimethylamino)ethyl]acridine-4-carboxamide, dihydrochloride, trihydrate

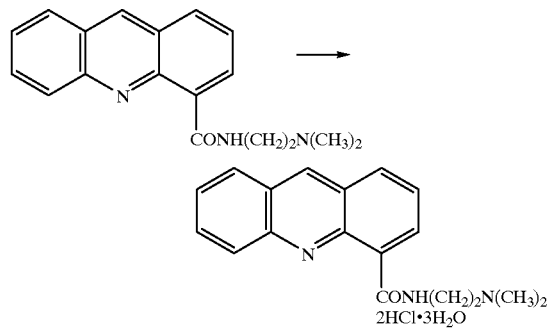

To the product of Example 5 (2.93 g, 100 mmol), dissolved in a mixture of toluene (20.7 ml) and EtOH (9 ml), was added dropwise concentrated HCl (2.0 ml, ca 200 mmol). Precipitation of the salt occurred which was completed by the addition of EtOAc (8.6 ml). The mixture was cooled to 5° C., stirred for a further 1 hour and the yellowish crystalline salt was filtered, washed with EtOAc(3×20 ml) and pulled dry on the filter to give the title compound 3.9 g (theory for 2HCl. 3H$_2$O, 4.2 g) Hplc indicated it was ca 98% a/a.

The salt was recrystallised by dissolving it in a mixture of EtOH (20 ml) and water (2 ml) at 70° C. The resultant solution was diluted with EtOAc (20 ml) maintaining the temperature of the mixture at ca 60–70° C. The mixture was then allowed to cool slowly to produce the dihydrochloride trihydrate as a yellowish crystalline solid which after cooling in an ice bath for 1 hour was filtered, washed with a chilled 10:10:1 mixture of EtOH:EtOAc:water (2×10 ml) and pulled dry on the filter. It was then allowed to equilibrate in a fume cupboard to constant weight to give the pure salt (3.6, 85.7%). Hplc, 99.2% a/a. $^1$HNMR (DMSO)δ2.90 (6H, s, N(CH$_3$)$_2$), 3.46 (2H, m, CH$_2$N(CH$_3$)$_2$), 3.98 (2H, m, CONHCH$_2$), 7.75 and 7.80 (2H, t and br.t, H-7 (7.75) and H-2 (7.80)), 8.02 (1H, m, H-6), 8.28 (1H,d, H-8), 8.46 (1H,d, H-1), 8.51 (1H, d, H-5), 8.77 (1H,d,H-3), 9.43 (1H,s, H-9), 10.65 (1H, br.s, NH$^+$(CH$_3$)$_2$), 11.45 (1H, br.t. CONH).

EXAMPLE 7

Preparation of [2-(dimethylamino)ethyl]acridine-4-carboxamide

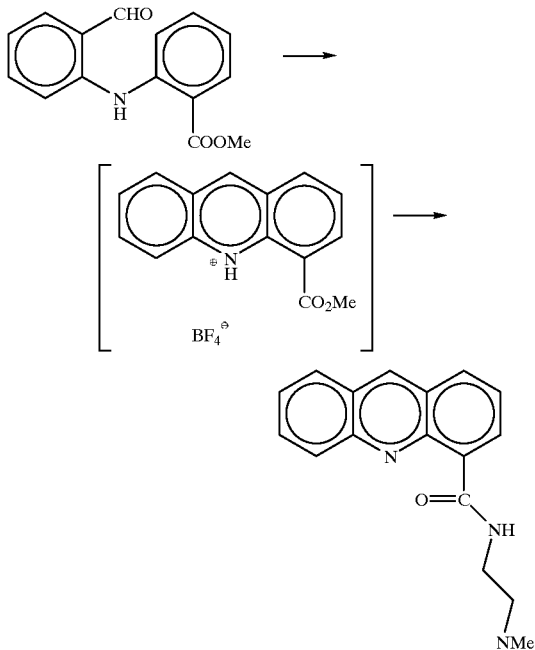

A stirred solution of the aldehyde produced in Example 3 (3.0 g; 11.76 mmole) in $CH_2Cl_2$ was saturated with nitrogen and boron trifluoride etherate (3.33 g; 23.5 mmole; 2 equivalents) was added dropwise under $N_2$. The solution became orange (a solid deposited which dissolved after 2–3 min), then clear dark red followed by a deposition of a yellow solid. It was left to stir for 4 hours until the reaction was complete by Tlc ($SiO_2$; $CH_3OH:CH_2Cl_2/1:40$). A solution of 1M $Na_2CO_3$ (15 ml) was added (pH 7) and the solution stirred for 5 min. The lower organic layer was separated, then washed with 1M $Na_2CO_3$ (15 ml). The combined aqueous layer was extracted with $CH_2Cl_2$ (10 ml), the organic layer was separated then added to the main organic layer. The combined organic layer was washed with brine (10 ml), reduced to ca ½ volume, then reevaporated from $CH_2Cl_2$ (20 ml). N,N-dimethylethylenediamine (NNDMEDA) was added (5.1 ml, 47.04 mmole, 4 equivalents) and the reaction mixture concentrated to remove any remaining $CH_2Cl_2$.

The residue was heated in an oil bath (110–120° C.) overnight Tlc ($SiO_2$; 10% $CH_3OH:CH_2Cl_2$) to give an orange/brown oil which was diluted with toluene (20 ml) then concentrated to low volume to remove excess NNDMEDA. The residue was diluted with EtOAc (25 ml) then washed with 1M $NaHCO_3$ solution (15 ml). The organic layer was separated, washed with water (2×10 ml) then separated. The combined organic layer was stirred with activated C (300 mg), Kieselguhr (300 mg) for 30 min, filtered through a dry Kieselguhr bed, washed with EtOAc and the filtrate concentrated to a gum (3.2 g) which rapidly crystallised. Upon trituration with EtOAc (2 ml) and hexane (20 ml) a yellowish-brown solid was obtained. The solid was filtered, washed with hexane then dried in vacuo (40° C.) to give the title compound (2.65 g; 77%) as a buff solid. $^1$HNMR data were obtained as reported for the product of Example 5.

EXAMPLE 8

Preparation of Compounds of Formula (I) from Compounds of Formula (VI).

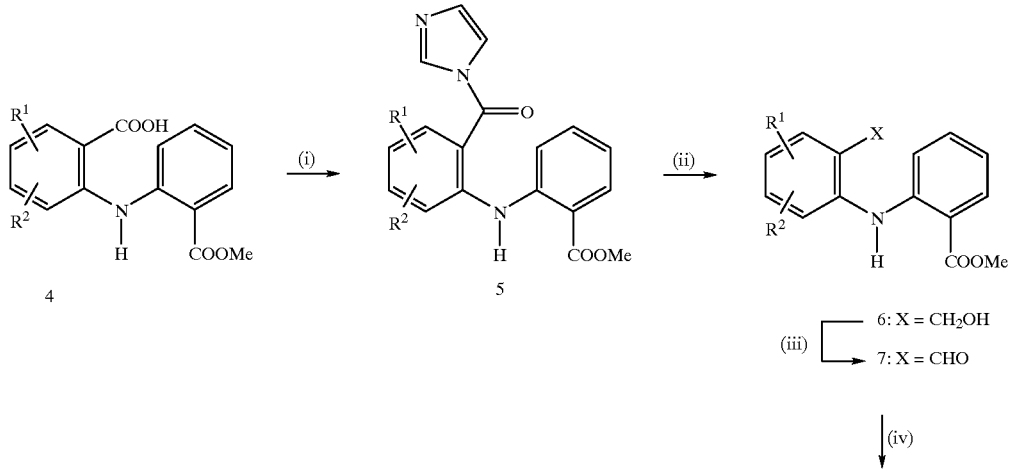

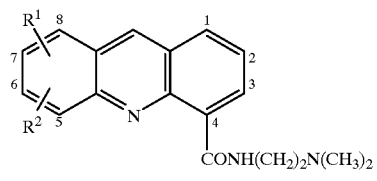

3

(v) ←

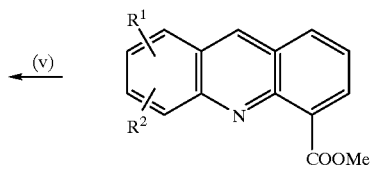

8

The series of reactions depicted in scheme 2 was carried out to produce DACA, compound 3a, and a series of analogues 3b to 3g. For each of these compounds the substituents $R^1$ and $R^2$ throughout scheme 2 had the following definitions

| $R^1$ | $R^2$ | Compounds |
|---|---|---|
| H | H | a |
| H | 5-$CF_3$ | b |
| H | 6-Me | c |
| H | 6-Er | d |
| H | 6-$CF_3$ | e |
| 6-Me | 7-Me | f |
| 7-Me | 5-Cl | g |

A solution of methyl 2-[N-(2-carboxyphenyl)amino]benzoate 4a,(10 g, 36.9 mmol) in dry THF (200 ml) was treated with 1,1-carbonyldiimidazole (8.97 g, 55.4 mmol). The reaction mixture was allowed to stir at room temperature for 15 hours, then the THF solution was added slowly to a suspension of $NaBH_4$ (7.00 g) in $H_2O$ (200 ml) without isolation of the intermediate imidazolide 5a. The reaction was virtually instantaneous and at the end of the addition the mixture was quenched with concentrated HCl, partitioned between $CH_2Cl_2$ (200 ml) and $NaHCO$, (200 ml), and the organic layer was dried with $Na_2SO_4$. Removal of the solvent and filtration of the residue through a plug of flash-grade silica gel in petroleum ether/EtOAc (4:1) gave methyl 2-[N-(2-hydroxymethyl)phenylamino]benzoate 6a (7.85 g, 83%). Mp ($CH_2Cl$/petroleum ether) 69–71° C. $^1H$ NMR $(CDCl)\delta1.93$ (br.s, 1H, OH), 3.91 (s, 3H, COOH $CH_3$), 4.72 (S, 2H, $CH,OH$), 6.74 (ddd, J=8.0, 7.0, 1.1 Hz, 1H, H-5), 7.08–7.44 (m, 6H, H-3,3', 4,4'5', 6'), 7.97 (dd, J=8.1, 1.6 Hz, 1H, H-6) 9.59 (br.s, 1H, NH).

A stirred solution of 6a (7.74 g, 30 mmol) in $Me_2CO$ (200 ml) was treated with a suspension of $MnO_2$ (10 g) for 3 days at room temperature. The $MnO_2$ was filtered off (Celite) and the $Me_2CO$ was removed under reduced pressure to yield methyl 2-[N-(2-formyl)phenylamino]benzoate 7a (7.70 g, 100%). A sample crystallised from EtOAc/petroleum ther had mp 110–112° C. $^1H$ NMR $(CDCl^2)\delta3.95$ (s, 3H, $OOCH_3$), 6.95–7.03 (m, 2H, H-4',5), 7.41–7.45 (m, 2H, H-5',6), 7.50 (br d, J=8.5 Hz, 1H, H-3 or H-6'), 7.61 (br d, J=8.2 Hz, 1H, H-6' or H-3), 7.65 (dd, J=7.7, 1.7 Hz, 1H, H-3'), 8.01 (dd, J=7.9. 1.7 Hz, 1H, H-6), 10.00 (s, 1H, CHO), 11.26 (br s, 1H, NH).

The aldehyde 7a (210 mg, 0.82 mmol) was placed in a flask which was flushed with $N_2$, then trifluoroacetic acid (10 mL) was added and the resultant solution was stirred for 24 hours at room temperature. Solvent was removed under reduced pressure to give crude methyl acridine-4-carboxylate 8a (183 mg. 94%). This was diluted with $CH_2Cl_2$ (100 mL), and neutralised with $Et_3N$. Solvents were removed under reduced pressure, and the residue was filtered through a short column of flash silica gel in EtOAc/petroleum ether (1:3) to give methyl acridine-4-carboxylate (8a) as an orange oil (1.83 g, 980%) $^1H$ NMR $(CDCl_3)\delta4.12$ (s, 3H, $COOCH_3$), 7.53–7.58 (m,2H,H-2 and H-6 or H-7), 7.79 (ddd, J=8.8, 6.6, 1.4 Hz, 1H, H-7 or H-6), 8.00 (dd, J=8.0, 1.0 Hz, 1H, H-1), 8.12–8.14 (m, 2H, H-5, 8), 8.30 (dd, J=8.7,0.9 Hz, 1H, H-3), 8.80 (s, 1H, H-9).

A solution of 8a (1.83 g, 7.72 mmol) and N,N-dimethylethylenediamine (3.40 g, 38.6 mmol) in propan-1-ol (80 ml) was flushed with $N_2$, and the mixture was heated at reflux for three days under $N_2$. Solvent was then removed under reduced pressure, and the residue was partitioned between $CH_2Cl_2$ (100 ml) and 1M $Na_2CO_3$ (100 ml). The organic layer was evaporated and the residue chromatographed on alumina, eluting with $CH_2Cl_2$/MeOH (199:1) to give N-[2-dimethylamino)ethyl]acridine-4-carboxamide 3a (1.38 g, 61%), mp (diHCl salt) 191–195° C., identical with an authentic sample.

An analogous procedure was employed to produce compounds 3b to 3g from the starting compounds 4b to 4g, respectively. All the compounds 3b to 3g had satisfactory spectroscopic and analytical properties. The yield of the intermediate aldehydes 7a to 7g from the starting compounds 4a to 4g (steps (i) and (ii)) were as follows:

| 4 | yield (4–7) | 7 |
|---|---|---|
| 4a | 83% | 7a |
| 4b | 100% | 7b |
| 4c | 82% | 7c |
| 4d | 67% | 7d |
| 4e | 77% | 7e |
| 4f | 60% | 7f |
| 4g | 44% | 7g |

EXAMPLE 9

Preparation of Acridine-4-carboxylic acid

To methyl acridine-4-carboxylate, prepared in Example 4,(183 mg), was added a degassed solution of NaOH in aqueous EtOH (1:1,2M)(35 ml). The mixture was stirred for 3 hours at 50° C., when a clear solution was obtained, then neutralised with glacial AcOH. Extraction with EtOAc (3×15 50 ml) followed by chromatography on silica gel, eluting with EtOAc/petroleum ether (1:4), gave acridine-4-carboxylic acid (160 mg, 87%), mp ($Me_2CO$) 196–197° C. (lit, mp 202–204° C.).

By the same procedure, other compounds of formula (III) were hydrolysed to the corresponding acridine-4-carboxylic acids.

EXAMPLE 10

Preparation of Compounds of Formula (I) from Acridine-4-carboxylic Acid Precursor General method A suspension of 7-ethylacridine-4-carboxylic acid, produced by the procedure of Example 9 from a compound of formula (III) wherein $R^1$ is H and $R^2$ is a 7-ethyl substituent (472 mg, 1.99 mmol), in dry DMF (10 ml) was stirred with 1-11'-carbonyldiimidazole (650 mg, 3.98 mmol) at 20° C. until homogeneous (ca. 12 h). The solution was then cooled to 0° C. and treated with N,N-dimethylethylenediamine (0.73 g, 9.96 mmol) for 5 min. Solvent was then removed under reduced pressure, and the residue was partitioned between $CH_2Cl_2$ (50 ml) and 1 M aqueous $K_2CO_3$ (30 ml). The organic layer was washed with water and evaporated, and the residue was chromatographed on alumina. Elution with $CH_2Cl_2$/MeOH (19:1) gave N-[2-(dimethylamino) ethyl]-7-ethylacridine-4-carboxamide (10a) as a yellow oil (288 mg, 48%). $^1$H NMR (CDCl$_3$)δ1.35 (t, J=7.6 Hz, 3H CH$_2$CH$_3$), 2.36 (s, 6H,N(CH$_3$)$_2$), 2.61 (t, J=6.1 Hz, 2H, CH$_2$N(CH$_3$)$_2$), 2.89 (q, J=7.6 Hz, 2H, CH$_2$CH$_3$), 3.63 (q, J=5.6 Hz, 2H, CH$_2$), 7.73 (dd, J=8.2, 7.2 Hz, 1H, H-2), 7.90 (dd, J=9.0, 1.9 Hz, 1H, H-6), 7.99 (br s, 1H, H-8), 8.18 (d, J=8.9 Hz, 1H, H-5), 8.34 (dd, J=8.5, 1.4 Hz, 1H, H-1), 8.73 (dd, J=7.1, 1.5 Hz, 1H, H-3), 9.21 (s, 1H, H-9), 11.81 (br t, J=4.7 Hz, 1H, CONH). Dihydrochloride salt, mp (EtOAc/MeOH) 173–175° C.

The general method above was used to produce the following compounds of formula (I):

N-[2-(Dimethylamino)ethyl-5-ethylacridine-4-carboxamide (compound 10b) (70%), mp (CH$_2$Cl$_2$/petroleum ether) 106–108° C.; dihydrochloride salt, mp (EtOAc/MeOH) 214–217° C.

N-[2-(Dimethylamino)ethyl]-5-isopropylacridine-4-carboxamide (compound 10c) as a yellow oil (76%), dihydrochloride salt, mp (EtOAc/MeOH) 213–215° C.

N-[2-(Dimethylamino)ethyl]-5-fluoroacridine-4-carboxamide (compound 1d) (73%), mp (hexane) 95–98.5° C.

N-[2-Dimethylamino)ethyl]-5-bromoacridine-4-carboxamide (compound 10e) (52%), mp 149–150° C., N-2-(Dimethylamino)ethyl]-5-trifluoromethylacridine-4-carboxamide (compound 10f) (74%). Hydrochloride salt, mp 207–211° C. (EtOAc/MeOH).

N-[2-(Dimethylamino)ethyl]-6-fluoroacridine-4-carboxamide (compound 10g) (87%), mp (dihydrochloride salt from MeOH/EtOAc) 203–204° C. (dec).

N-[2-(Dimethylamino)ethyl]-6-bromoacridine-4-carboxamide (compound 10h) (676), mp (dihydrochloride salt from MeOH/EtOAc) 161–163° C.

N-[2-(Dimethylamino)ethyl]-7-isopropylacridine-4-carboxamide (compound 10i), as a yellow oil (97%), dihydrochloride salt, mp (MeOH/EtOAc) 182–187° C.

N-[2-(Dimethylamino)ethyl]-7-t-butylacridine-4-carboxamide (compound 10j) (92%), mp (CH$_2$Cl$_2$/petroleum ether) 128–129° C.

N-[2-(Dimethylamino)ethyl]-7-phenylacridine-4-carboxamide (compound 10k) (64%), mp (CH$_2$Cl$_2$/petroleum ether) 115–116.5° C., hydrochloride salt, mp (MeOH/EtOAc) 83–85° C.

N-[2-Dimethylamino)ethyl]-7-fluoroacridine-4-carboxamide (compound 10l) (74%), mp (MeOH/EtOAc) 128.5–130° C.

N-[2-(Dimethylamino)ethyl]-7-bromoacridine-4-carboxamide (compound 10m), (84%), mp (dihydrochloride salt from MeOH.EtOAc) 181.5–183° C.

EXAMPLE 11

Preparation of Compounds of Formula (I) from Methyl Acridine-4-carboxylate Precursor General Method A solution of the aldehyde methyl 2-[N-(2-formylphenyl) amino]benzoate (2 g, 7.84 mmol) in trifluoroacetic acid (TFA)(20 ml) was degassed and placed in a two-necked flask which was then flushed with $N_2$. The solution was stirred for 15 hours at room temperature under $N_2$, and the TFA was then removed under reduced pressure. The resulting oil was diluted with $CH_2Cl_2$ (100 ml), and the solution was neutralised with Et$_3$N. Solvents were removed under reduced pressure, and the residue was filtered through a short column of flash silica gel in EtOAc/petroleum ether (1:3) to give methyl acridine-4-carboxylate as an orange oil (1.83 g, 98%). $^1$H NMR (CDCl$_3$)δ4.12 (s, 3H, CO$_2$CH$_3$), 7.53–7.58 (m, 2H, H-2 and H-6 or H-7), 7.79 (ddd, J=8.8, 6.6, 1.4 Hz, 1H, H-7 or H-6), 8.00 (dd, J=8.0, 0.8 Hz, 1H, H-1), 8.12–8.14 (m,2H, H-5,8), 8.30 (dd, J=8.7, 0.8 Hz, 1H, H-3), 8.80 (s, 1H, H-9).

A solution of methyl acridine 4-carboxylate (1.83 g, 7.72 mmol) and N,N-dimethylethylenediamine (3.40 g, 38.6 mmol) in n-propanol (80 ml) was flushed with $N_2$, and the mixture was heated at reflux for three days under $N_2$. Solvent was then removed under reduced pressure, and the residue was partitioned between $CH_2Cl_2$ (100 ml) and 1M $Na_2CO_3$ (100 ml). The organic layer was evaporated and the residue chromatographed on alumina, eluting with $CH_2Cl_2$/MeOH (199:1) to give N-[2-(dimethylamino)ethyl]acridine-4-carboxamide (DACA) (1.47 g, 61%), mp (dihydrochloride salt from MeOH/EtOAc) 162–165° C.

The general method above was used to produce the following compound of formula (I):

N-[2-(Dimethylamino)ethyl]-6-trifluoromethylacridine-4-carboxamide (compound 11a) (92%), mp. (MeOH/EtOAc) 188–189.5° C.

EXAMPLE 12

Pharmaceutical Composition

Tablets, each weight 0.15 g and containing 25 mg of one of the compounds of formula (I) can be manufactured as follows:

Composition for 10,000 Tablets

Compound of formula (I) (250 g)

lactose (800 g)

corn starch (415 g)

talc powder (30 g)

magnesium stearate (5 g)

The compound of formula (I), lactose and half the corn starch are mixed. The mixture is then forced through a sieve 0.5 mm mesh size. Corn starch (10 g) is suspended in warm water (90 ml). The resulting paste is granulated to a powder. The granulate is dried and comminuted on a sieve of 1.4 mm mesh size. The remaining quantity of starch, talc and magnesium stearate is added, carefully mixed and processed into tablets.

We claim:

1. A process for producing an acridine carboxamide of formula (I):

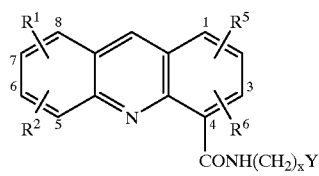
(I)

wherein each of $R^1$, $R^2$, $R^5$ and $R^6$, which may be the same or different, is H, $C_1$–$C_6$ alkyl, $C_1$–$C_6$ alkoxy, aryloxy, aralkyloxy, halogen, phenyl, $CF_3$, $NO_2$, $NH_2$, $N(R)_2$, NHCOR, NHCOOR, $NHR^4$, OH, SH, SR or $SR_2$, wherein $R^4$ is H, COR, $SO_2R$, COPh, $SO_2Ph$ or $C_1$–$C_6$ alkyl which is unsubstituted or substituted by OH or amino, and R is $C_1$–$C_6$ alkyl; or $R^1$ and $R^2$, or $R^5$ and $R^6$, together form a methylenedioxy group; x is an integer of 1 to 6 and Y is $N(R)_2$ as defined above; or a pharmaceutically acceptable salt thereof, which process comprises:

(a) cyclizing a compound of formula (II):

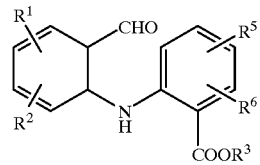
(II)

wherein $R^1$, $R^2$, $R^5$ and $R^6$ are as defined above and R3 is $C_1$–$C_6$ alkyl, aryl or aryl-$C_1$–$C_3$ alkyl, by treatment with boron trifluoride or a complex thereof to obtain a tetrafluoroborate salt of formula (IIIa):

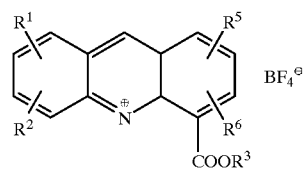
(IIIa)

wherein $R^1$, $R^2$, $R^3$, $R^5$ and $R^6$ are as defined above, followed by treatment of the salt with an inorganic base in EtOAc or $CH_2Cl_2$ to generate a compound of formula (III);

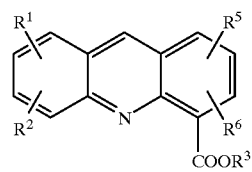
(III)

wherein $R^1$, $R^2$, $R^3$, $R^5$ and $R^6$ are as defined above; and (b) treating either
 (i) the compound of formula (III) as defined above with a primary alkylamine of formula (IV):

$NH_2(CH_2)_2Y$ (IV)

wherein x and Y are as defined above; or (ii) the carboxylic acid obtainable by hydrolyzing the compound of formula (III) as defined above, under basic conditions, with a primary alkyl amine of formula (IV) as defined above in the presence of a suitable coupling agent, to obtain a compound of formula (I) as defined above, and (c) if desired, converting one compound of formula (I) into another compound of formula (I), and/or converting a compound of formula (I) into a pharmaceutically acceptable salt thereof.

2. A process for producing N-[2-(dimethylamino)ethy] acridine-4-carboxamide (DACA) of the following formula:

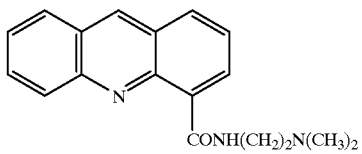

which process comprises
 (i) treating a compound of formula (VI):

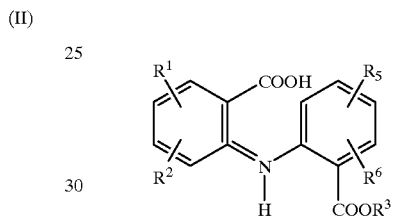
(VI)

wherein $R^1$, $R^2$, $R^5$ and $R^6$ are H and $R^3$ is $C_1$–$C_6$ alkyl, aryl-$C_1$–$C_3$ alkyl or aryl with 1,1'-carbonyldiimidazole in an organic solvent to obtain a compound of formula (VII):

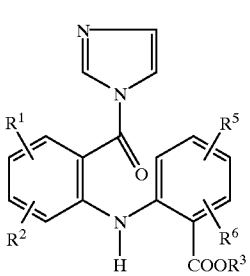
(VII)

wherein $R^1$, $R^2$, $R^5$ and $R^6$ are H and $R^3$ 3 is as defined above;

(ii) treating the compound of formula (VII) as defined above with sodium borohydride in the presence of water to obtain a compound of formula (V):

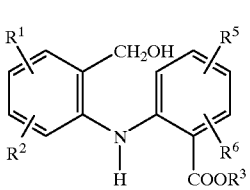
(V)

wherein $R^1$, $R^2$, $R^5$ and $R^6$ are H and $R^3$ is as defined above;

(iii) oxidizing the compound of formula (V) as defined above to obtain a compound of formula (II):

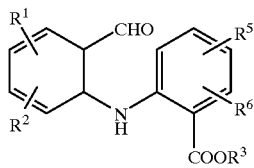
(II)

wherein $R^1$, $R^2$, $R^5$ and $R^6$ are H and $R^3$ is as defined above;

(iv) cyclizing the compound of formula (II) as defined above by treatment with boron trifluoride or a complex thereof to obtain a tetrafluoroborate salt of formula (IIIa):

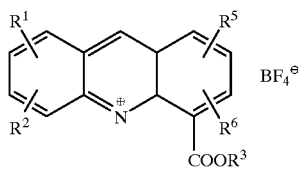
(IIIa)

wherein $R^1$, $R^2$, $R^3$, $R^5$ and $R^6$ are H and $R^3$ are as defined above, followed by treatment of the salt with an inorganic base in EtOAc or CH2C12 to generate a compound of formula (III):

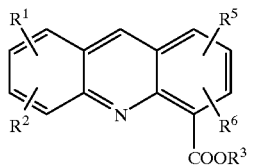
(III)

wherein $R^1$, $R^2$, $R^5$ and $R^6$ are H and $R^3$ is as defined above; and (v) treating the compound of formula (III) as defined above with a primary alkylamine of formula (IV):

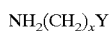 (IV)

wherein x is 2 and Y is N(CH$_3$)$_2$, to obtain DACA.

3. A process according to claim 1 wherein $R^1$, $R^2$, $R^5$ and $R^6$ in formula (II) are H, and in formula (IV) x is 2 and Y is N(CH$_3$)$_2$, such that the acridine carboxamide of formula (I) produced is N-[2-(dimethylamino)ethyl]acridine-4-carboxamide.

4. A process according to claim 1 which further comprises producing the compound of formula (II) by oxidising the corresponding alcohol of formula (V):

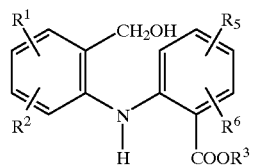
(V)

wherein $R^1$, $R^2$, $R^3$, $R^5$ and $R^6$ are as defined in claim 1.

5. A process according to claim 4 which comprises producing the alcohol of formula (V) by (a) treating a compound of formula (VI):

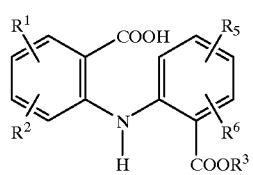
(VI)

wherein $R^1$, $R^2$, $R_3$, $R^5$ and $R^6$ are as defined in claim 1, with 1,1'-carbonyldiimidazole in a polar solvent, to obtain a compound of formula (VII):

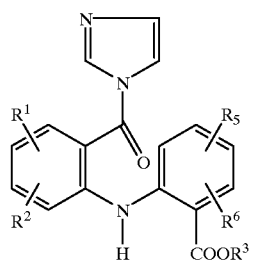
(VII)

wherein $R^1$, $R^2$, $R^3$, $R^5$ and $R^6$ are as defined in claim 1, and (b) reducing the compound of formula (VII) as defined above.

6. A process according to claim 5 which further comprises producing the compound of formula (VI) by heating together a mixture of an anthranilic acid of formula (VIII):

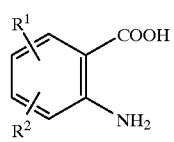
(VIII)

wherein $R^1$ and $R^2$ are as defined in claim 1, and a 2-iodobenzoic acid ester of formula (IX):

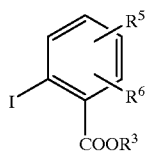
(IX)

wherein $R^3$, $R_5$ and $R^6$ are as defined in claim 1, in the presence of a copper catalyst and a base in a polar solvent.

7. A process according to claim 2 which further comprises producing the compound of formula (VI) by heating together anthranilic acid of formula (VIII):

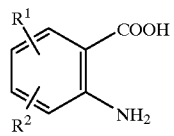
(VIII)

wherein $R^1$ and $R^2$ are as defined in claim 2, and a 2-iodobenzoic acid ester of formula (IX):

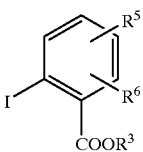
(IX)

wherein $R^3$, $R^5$ and $R^6$ are as defined in claim 2, in the presence of a copper catalyst and a base in a polar solvent.

8. A process according to claim 2 or 7 which further comprises converting DACA into a pharmaceutically acceptable salt thereof.

9. A process according to claim 1 or claim 2 which further comprises formulating the compound of formula (I) or DACA, or a pharmaceutically acceptable salt of a compound of formula (I) or DACA, with a pharmaceutically acceptable carrier or diluent.

10. A process according to claim 1 or claim 2 wherein the complex of boron trifluoride is the acetic acid complex.

11. A process according to claim 1 or claim 2 wherein the boron trifluoride is used in the form of its etherate BF3O (Et)2.

* * * * *